US008852247B2

(12) United States Patent
Abdelgany (10) Patent No.: US 8,852,247 B2
(45) Date of Patent: Oct. 7, 2014

(54) ORTHOPEDIC ANTI BACK-OUT MECHANISM

(75) Inventor: Mahmoud F. Abdelgany, Rockaway, NY (US)

(73) Assignee: Custom Spine, Inc., Parsippany, NJ (US)

( * ) Notice: Subject to any disclaimer, the term of this patent is extended or adjusted under 35 U.S.C. 154(b) by 1535 days.

(21) Appl. No.: 11/952,351

(22) Filed: Dec. 7, 2007

(65) Prior Publication Data

US 2009/0149888 A1 Jun. 11, 2009

(51) Int. Cl.
*A61B 17/80* (2006.01)
*A61B 17/70* (2006.01)

(52) U.S. Cl.
CPC ......... *A61B 17/7059* (2013.01); *A61B 17/8042* (2013.01)
USPC ........................................... 606/290; 606/286

(58) Field of Classification Search
USPC ............... 606/70–71, 280–299, 902–906, 606/300–331; 411/103, 107, 109, 166
See application file for complete search history.

(56) References Cited

U.S. PATENT DOCUMENTS

| 4,388,921 | A | * | 6/1983 | Sutter et al. ...................... 606/71 |
| 4,408,601 | A | * | 10/1983 | Wenk ............................. 606/282 |
| 4,696,611 | A | * | 9/1987 | Guay ............................. 411/103 |
| 4,789,287 | A | * | 12/1988 | Le ................................. 411/107 |
| 5,876,402 | A | * | 3/1999 | Errico et al. ..................... 606/287 |
| 7,048,739 | B2 | * | 5/2006 | Konieczynski et al. ....... 606/288 |
| 7,137,984 | B2 |   | 11/2006 | Michelson |
| 8,747,443 | B2 | * | 6/2014 | Aferzon ......................... 606/295 |
| 2002/0151899 | A1 | * | 10/2002 | Bailey et al. .................... 606/69 |
| 2003/0187442 | A1 | * | 10/2003 | Richelsoph et al. ............. 606/70 |
| 2003/0225409 | A1 | * | 12/2003 | Freid et al. ...................... 606/69 |
| 2004/0127899 | A1 | * | 7/2004 | Konieczynski et al. ......... 606/69 |
| 2005/0043736 | A1 | * | 2/2005 | Mathieu et al. ................. 606/73 |
| 2005/0251137 | A1 | * | 11/2005 | Ball ................................. 606/61 |
| 2006/0235402 | A1 | * | 10/2006 | Celli et al. ....................... 606/69 |
| 2007/0123879 | A1 | * | 5/2007 | Songer et al. ................... 606/69 |

* cited by examiner

*Primary Examiner* — Nicholas Woodall
*Assistant Examiner* — Larry E Waggle, Jr.
(74) *Attorney, Agent, or Firm* — Rahman LLC (57) ABSTRACT

A bone plate that is inserted into a vertebral column includes a hole, an eccentrically-shaped annulus, and a channel. The hole includes an eccentrically-shaped sidewall and the annulus includes an aperture positioned on an upper surface of the annulus. The hole is configured to receive a bone screw. The channel is positioned adjacent to the sidewall and adapted to hold the annulus. The channel may permit the annulus to rotate with respect to the sidewall. The channel may include a notch and the annulus may include a flared end. The flared end may be adapted to fit into the notch of the channel. A portion of the annulus may be adapted to cover a portion of the bone screw. As the annulus rotates with respect to the sidewall, the portion of the annulus may cover the portion of the bone screw.

17 Claims, 8 Drawing Sheets

ORTHOPEDIC ANTI BACK-OUT MECHANISM

BACKGROUND

1. Technical Field

The embodiments herein generally relate to medical devices, and, more particularly, to an anti back-out mechanism used during orthopedic surgeries.

2. Description of the Related Art

Cervical spinal fusion surgeries are often carried out to eliminate motion at a vertebral segment. These fusions may also prevent the spine from falling into a collapsed deformity (e.g., kyphosis). Incisions are made in the front of the neck in anterior cervical fusions. These fusions remove pressure from the nerve roots caused by bone spurs or a herniated disc. Anterior cervical spinal fusion surgeries are commonly performed in conjunction with anterior cervical discectomy (e.g., removing the disc). In addition, anterior cervical spinal fusions are carried out to treat cervical instability due to trauma (fractures or dislocations), tumor, and infections, etc.

It is also necessary to secure and stabilize the cervical vertebrae during spinal fusion surgeries. Stabilization leads to an appropriate healing or a preferred result. To accomplish this, a cervical plate is mounted on one or more vertebrae during the surgery. The plates should be firmly secured to the spinal column so that the plates are not tattered out when they are stressed and they should be capable of placement and fixation in a manner that is convenient for the surgeon. Typically, screws are used to mount the cervical plate to the one or more vertebrae. It is important to properly align the plate on the vertebrae for receipt of mounting screws during a mounting process.

The interface between the screws and the bone presents some problems of stability. Due to anatomical forces on the skeleton the screws securing the plate to the cervical spine loosen over time resulting in movement of the screw, and back out of the plate or bones. This is usually termed as "back-out", and it can lead to increased pain, infection, and/or possible death of the patient.

Conventional devices typically do not inhibit backing out of the bone screws. Threaded screws with heads that engage threads in the cervical plate to lock the screws in the plate are available. However, these systems generally do not provide adequate locking of the screw to the plates, leading to loosening of screws over time. Most cervical plates incorporate a built-in expanding ring that expands to allow a bone screw to go through, and collapse after passing the screw through the ring to prevent the screw from backing out over time. In these designs, particularly as the rings are small in size, it generally cannot be detected whether the rings have secured the screw. Further, adjustments in the fitting of the cervical plate typically cannot be made due to poor visibility and control. Accordingly, there remains a need for a new orthopedic anti-back out mechanism to secure and stabilize the vertebral column.

SUMMARY

In view of the foregoing, an embodiment herein provides a new orthopedic anti-back out mechanism to secure and stabilize a vertebral column. The orthopedic anti-back out mechanism includes a bone plate to be inserted into the vertebral column. The bone plate includes a hole, an eccentrically-shaped annulus, and a channel. The hole includes an eccentrically-shaped sidewall and the annulus includes an aperture positioned on an upper surface of the annulus. The sidewall may be angled. The annulus is rotatably seated adjacent to the sidewall in the hole. The hole is configured to receive a bone screw. The channel may be positioned adjacent to the sidewall and adapted to hold the annulus. The channel may permit the annulus to rotate with respect to the sidewall. The channel may include a notch and the annulus may include a flared end. The flared end may be adapted to fit into the notch of the channel. A portion of the annulus may be adapted to cover a portion of the bone screw. As the annulus rotates with respect to the sidewall, the portion of the annulus may cover the portion of the bone screw.

Another aspect provides a system for providing stability to a vertebral column. The system includes a plate structure. The plate structure includes a hole, an eccentrically-shaped annulus, a channel, and a tool. The hole includes an eccentrically-shaped sidewall. The sidewall may be angled. The eccentrically-shaped annulus is rotatably seated adjacent to the sidewall in the hole. The annulus includes an aperture positioned on an upper surface of the annulus. The hole is configured to receive a bone screw and the tool is adapted to rotate the annulus.

The channel may be positioned adjacent to the sidewall. The channel may be adapted to hold the annulus and may permit the annulus to rotate with respect to the sidewall. The channel may include a notch and the annulus may include a flared end. The flared end of the annulus may be adapted to fit into the notch of the channel. A portion of the annulus may be adapted to cover a portion of the bone screw. As the annulus rotates with respect to the sidewall, the portion of the annulus may cover the portion of the bone screw. The plate structure may include any of a cervical bone plate, an anterior lumbar plate, and a lateral lumbar plate. The tool may include a cylindrical rod portion and a circular head positioned at an end of the cylindrical rod portion. A peg and an annular ring may be positioned on the circular head. The peg of the tool may be adapted to fit into the aperture of the annulus. The annular ring may be adapted to fit in the annulus, and the rotation of the tool may cause the peg to rotate the annulus.

In yet another aspect, a method of performing a surgical procedure includes attaching a bone plate to a vertebral column, inserting a bone screw in an annulus in a hole, securing the bone screw to the vertebral column, rotating the annulus, and terminating rotation of the annulus when a portion of the annulus covers a portion of the bone screw. The bone plate includes the hole and the eccentrically-shaped annulus. The hole includes an eccentrically-shaped sidewall. The eccentrically-shaped annulus is seated adjacent to the sidewall in the hole. As the annulus rotates, the portion of the annulus may cover the portion of the bone screw.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new orthopedic anti-back out mechanism to secure and stabilize the vertebral column. The embodiments herein achieve this by providing a bone plate 100 to be inserted in a vertebral column (not shown), wherein the bone plate 100 includes a hole 114 and an eccentrically-shaped annulus 116. The hole 114 includes an eccentrically-shaped sidewall and the annulus 116 includes an aperture 118 positioned on an upper surface of the annulus 116. The annulus 116 is rotatably seated adjacent to the sidewall in the hole 114. The hole 114 is configured to receive a bone screw 120. Referring now to the drawings, and more particularly to FIGS. 1 through 5, where similar reference characters denote corresponding features consistently throughout the figures, there are shown preferred embodiments.

Figure 1:
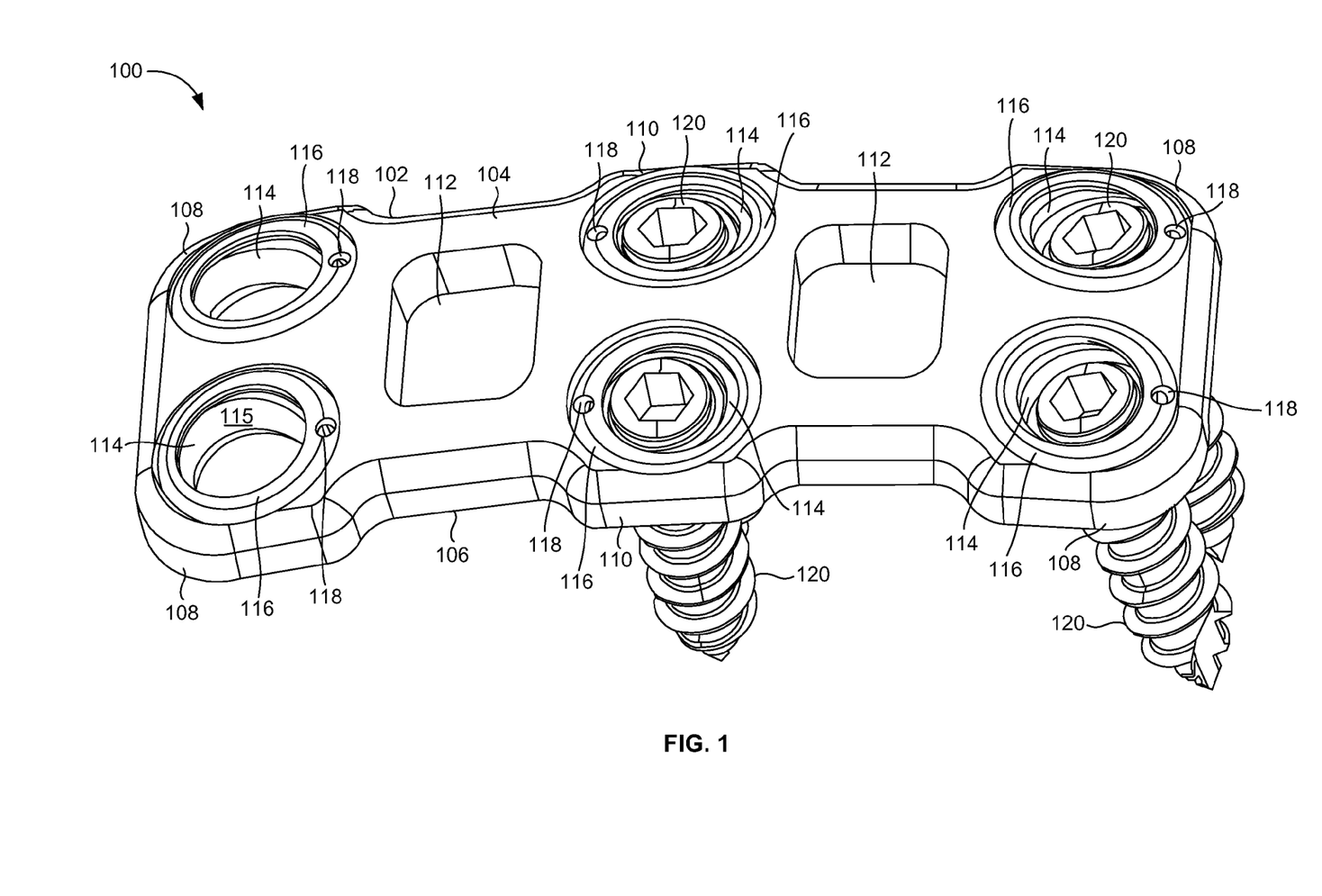
FIG. 1 illustrates a perspective view of a bone plate with an anti back-out mechanism according to an embodiment herein.

FIG. 1 illustrates a perspective view of a bone plate 100 with an anti back-out mechanism 116 according to an embodiment herein. The bone plate 100 includes a rectangular plate 102, a top surface 104, a bottom surface 106, rounded corners 108, projections 110, openings 112, holes 114 to accommodate bone screws 120, eccentrically-shaped anti back-out rings 116, and apertures 118. The curved structure of the rectangular plate 102 complements the natural curved structure of a vertebral body (not shown). The projections 110 are positioned at a substantially central area of the rectangular plate 102. The projections 110 along with the rounded corners 108 provide additional strength in a region surrounding each of the bone screws 120.

The openings 112 are adapted for visualization of bone graft material once the bone plate 100 is inserted into the vertebral body. While only four bone screws 120 are illustrated in FIG. 1, those skilled in the art would understand that the bone plate 100 may include more than four bone screws 120 as all of the holes 114 are adapted to accommodate their own bone screw 120. Each of the holes 114 includes an angled eccentrically-shaped sidewall 115. The eccentrically-shaped anti back-out rings 116 are rotatably seated adjacent to the eccentrically shaped sidewall 115 in the holes 114. A portion of each of the anti back-out rings 116 is adapted to cover a portion of the bone screws 120. The anti back-out rings 116 enable a head of the bone screws 120 to fit into the holes 114 and thus prevent the bone screws 120 from reverse threading and/or backing out of the bone plate 100. The apertures 118 are positioned on an upper surface 211 (best shown in FIG. 3B) of each of the anti back-out rings 116. The bone screws 120 may be fixed in a fixed angle or a variable angle (best shown in FIGS. 3A through 3C). The bone screws 120 being fitted through the holes 114 are anchored into the vertebral body. In a preferred embodiment, once the bone screws 120 are driven into the bone plate 100 and the vertebral body, the anti back-out rings 116 are then rotated with respect to channels 302 (best shown in FIGS. 3A through 3C) adjacent to the sidewalls 115 to cover a portion of the bone screws 120 to prevent their possible back-out from the plate 100 unless desired by the surgeon.

Figure 2A:
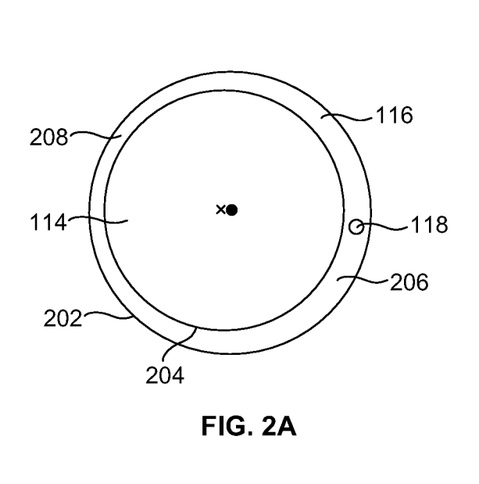
FIG. 2A illustrates an isolated top view of the anti back-out mechanism of FIG. 1 in an unlocked configuration according to an embodiment herein.

FIG. 2A illustrates an isolated top view of one anti back-out ring 116 in an unlocked configuration according to an embodiment herein. From this view, the anti back-out ring 116 is seen as including two circles 202, 204, a thick end 206, and a thin end 208. As shown, the ring 116 has an eccentric shape in terms of the non-uniform width of the ring 116. In other words, the circles 202, 204 defining the ring 116 are not concentric (i.e., the circles 202, 204 do not share the same center point). As shown in FIG. 2A, the center point of the outer circle 202 of the ring 116 is denoted by the dot, and the center point of the inner circle 204 of the ring 116 is denoted by the 'x' mark. Accordingly, due to the eccentric shape, the ring 116 has the thick end 206 that gradually becomes the thin end 208.

Figure 2B:
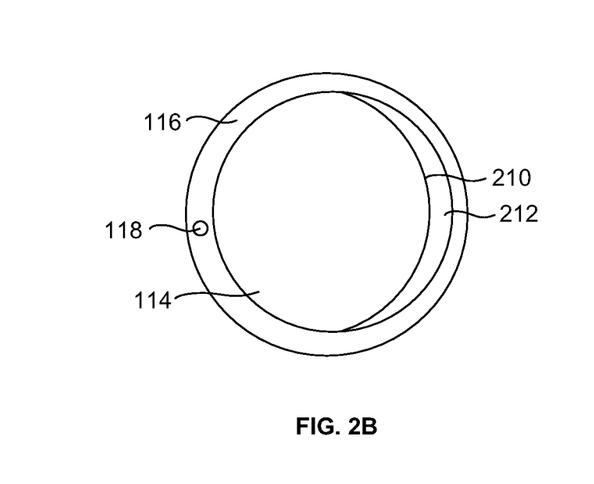
FIG. 2B illustrates an isolated top view of the anti back-out mechanism of FIG. 1 in a locked configuration according to an embodiment herein.

FIG. 2B illustrates an isolated top view of the anti back-out ring 116 in a locked configuration according to an embodiment herein. The anti back-out ring 116 sits above a sidewall base 210 having a top surface 212. The locking occurs by rotating the ring 116 in either a clockwise or counter-clockwise rotation. The thicker end 206 is rotated 180° (and correspondingly the thin end 208 also rotates 180°) thereby exposing the underlying top surface 212 of the sidewall base 210. Moreover, the sidewall base 210 is also configured in an eccentric shape such that it has a non-uniform width to match the non-uniform width of the ring 116. Accordingly, the sidewall base 210 also has a similarly configured thick end 206 and the thin end 208 (as further illustrated in FIG. 3B).

Figure 2C:
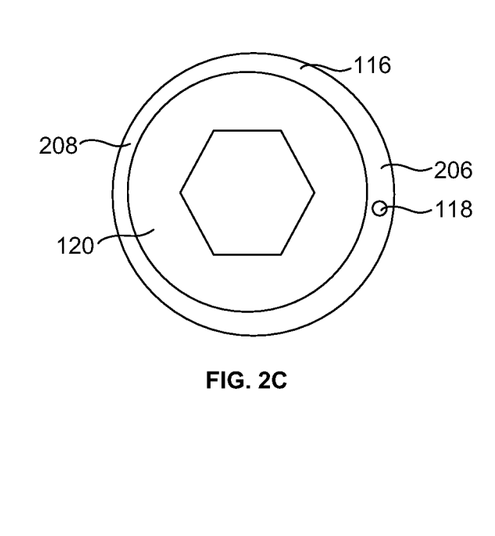
FIG. 2C illustrates an isolated top view of the anti back-out mechanism of FIG. 2A with an inserted bone screw in an unlocked configuration according to an embodiment herein.
Figure 2D:
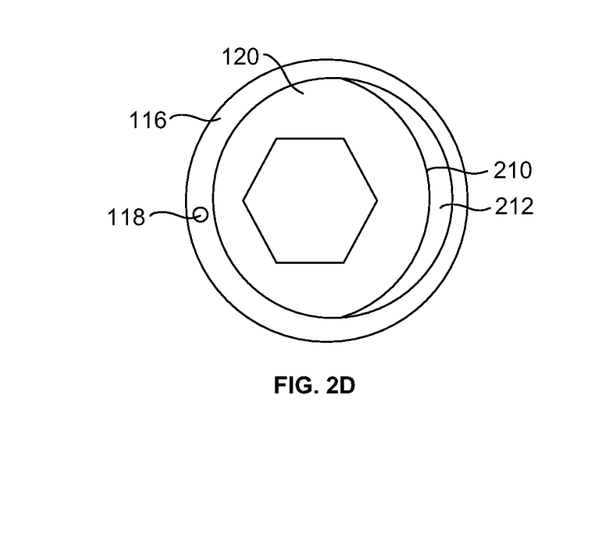
FIG. 2D illustrates an isolated top view of the anti back-out mechanism of FIG. 2B with an inserted bone screw in a locked configuration according to an embodiment herein.

FIG. 2C illustrates an isolated top view of the anti back-out ring 116 of FIG. 2A with an inserted bone screw 120 in an unlocked configuration according to an embodiment herein. The bone screw 120 is able to fit within the space defined by the inside of the ring 116. Once the bone screw 120 is seated in the ring 116 it may be locked. Accordingly, FIG. 2D illustrates an isolated top view of the anti back-out ring 116 of FIG. 2B with the inserted bone screw 120 in a locked configuration according to an embodiment herein. As shown, the ring 116 has been rotated 180° to reveal the underlying top surface 212 of the sidewall base 210. Because the thick end 206 of the ring 116 now covers a portion of the bone screw 120, the ring 116 prevents the bone screw 120 from backing out, thereby locking the bone screw 120 in the ring 116.

Figure 3A:
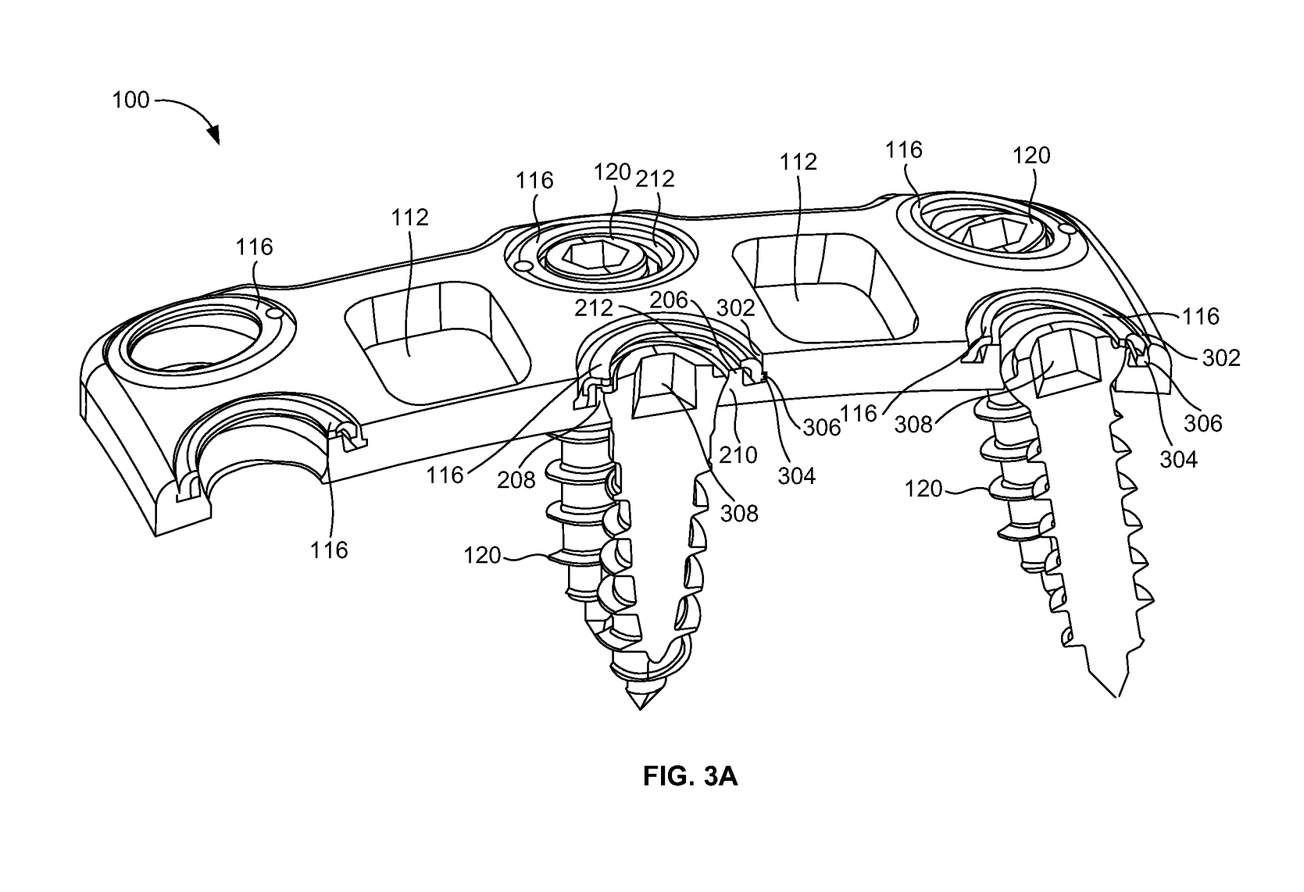
FIG. 3A illustrates a sectional view of the bone plate and anti back-out mechanism of FIG. 1 according to an embodiment herein.
Figure 3B:
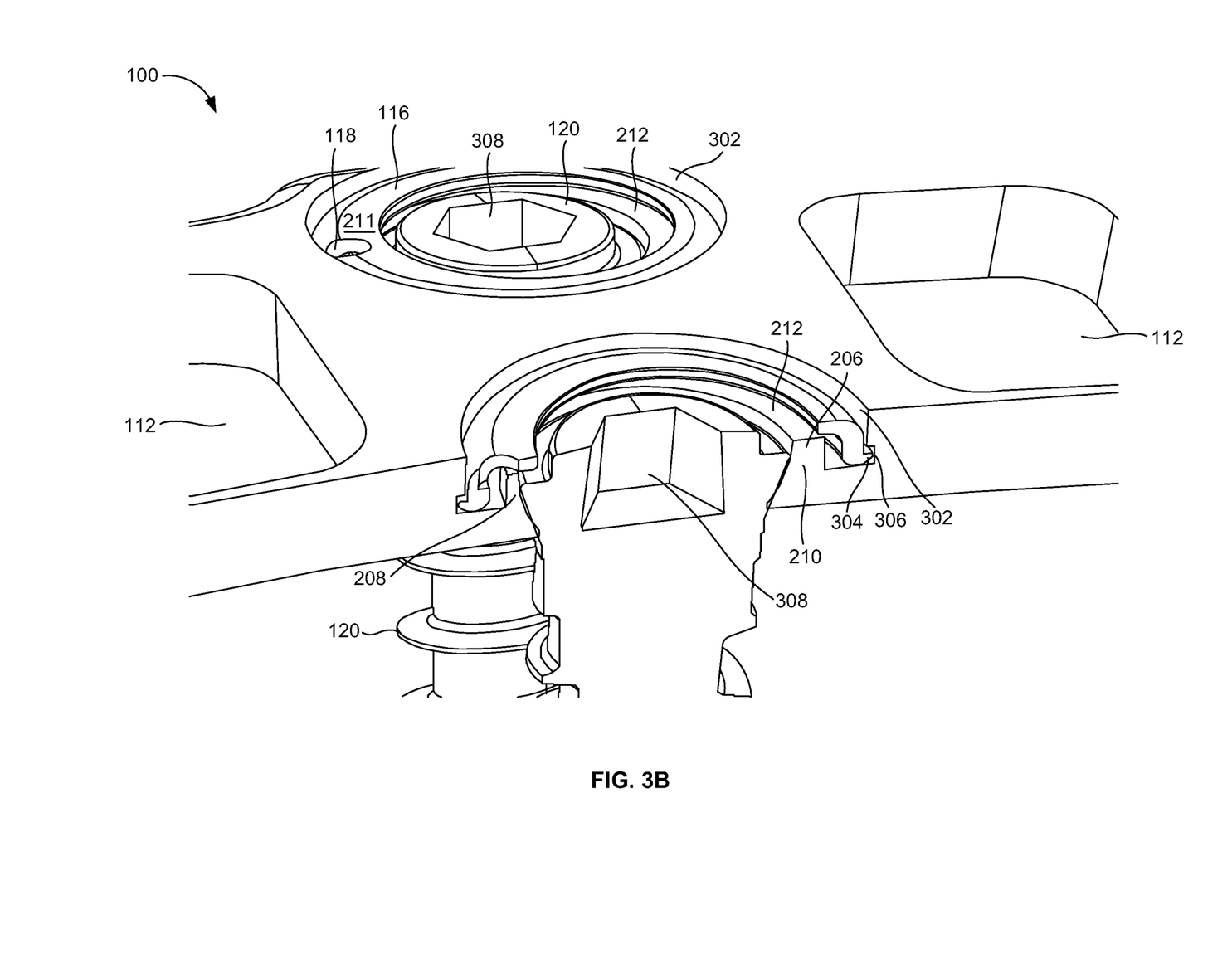
FIGS. 3B and 3C illustrate magnified views of the bone plate and anti back-out mechanism of FIG. 3A in different modes of operation according to an embodiment herein.
Figure 3C:
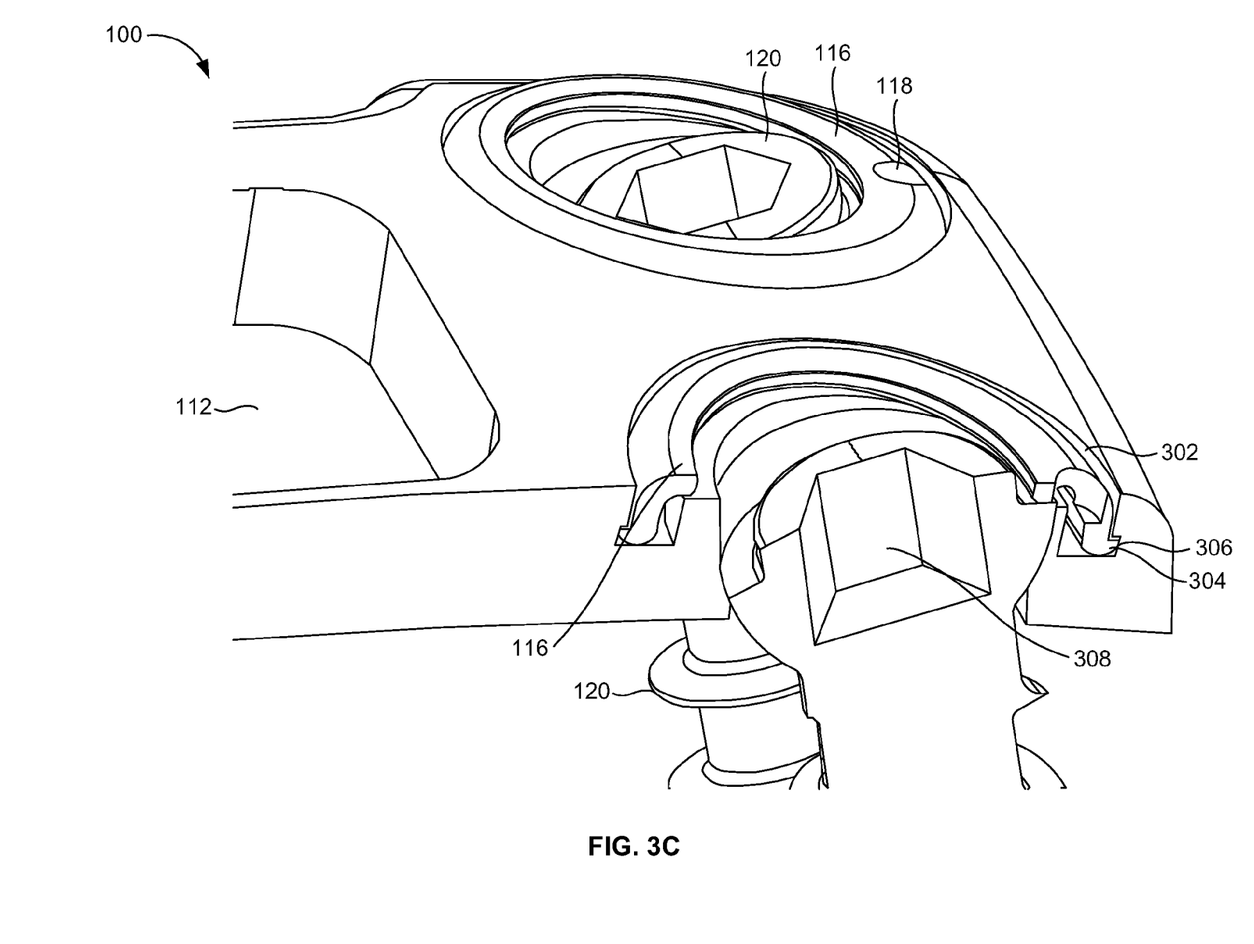

FIG. 3A illustrates a sectional view of the bone plate 100 and anti back-out mechanism 116 of FIG. 1 according to an embodiment herein. FIGS. 3B and 3C illustrate magnified views of the bone plate 100 and anti back-out mechanism 116 of FIG. 3A. The bone plate 100 includes channels 302. Each of the anti back-out rings 116 includes a flared end 304. Similarly, each of the channels 302 includes a notch 306. The channels 302 are positioned adjacent to the sidewall 115 of the holes 114 and are adapted to hold the anti back-out rings 116. The channels 302 permit the anti back-out rings 116 to rotate with respect to the sidewall 115 of the holes 114. Each flared end 304 of each of the anti back-out rings 116 is positioned at a bottom of each of the anti back-out rings 116. Similarly, each notch 306 is positioned at a bottom of each of the channels 302. Furthermore, each flared end 304 is adapted to fit into the notch 306 of the channel 302. Moreover, each bone screw 120 includes an internal chamber 308 which is positioned on a head of each of the bone screws 120. The internal chamber 308 is configured (although a hex configuration is illustrated in the drawings, those skilled in the art would understand that any suitable configuration is adaptable in accordance with the embodiments herein) to allow a surgical tool (not shown) to drive the bone screws 120 into the vertebral column. FIG. 3B illustrates the bone screws 120 in a non-angled orientation, while FIG. 3C illustrates the bone screws 120 positioned at an angle. However, even in the angled orientation, the rings 116 prevent the bone screws 120 from backing out of the plate 100 once the rings 116 are rotated into their locked configuration.

Figure 4A:
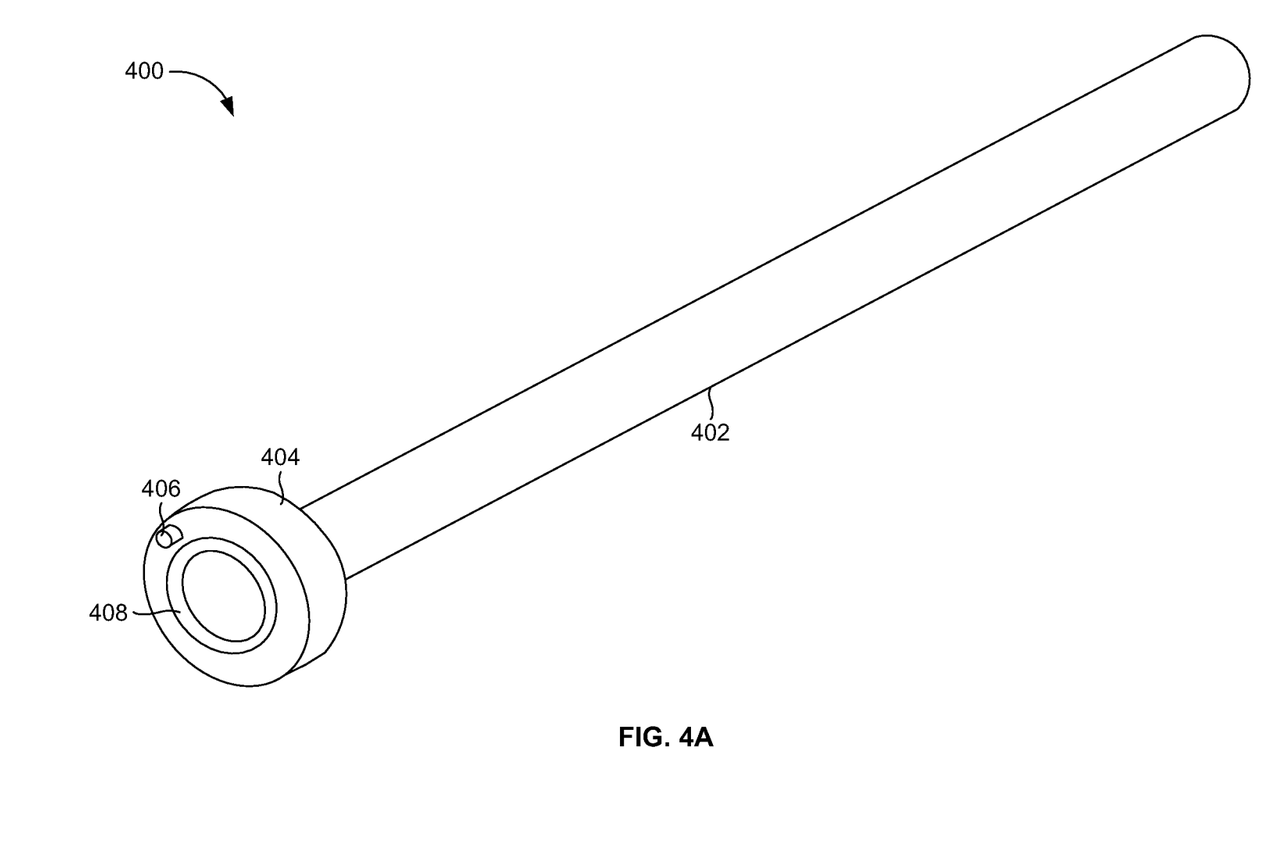
FIG. 4A illustrates a perspective view of a tool used in accordance with the anti back-out mechanism of FIG. 1 according to an embodiment herein.
Figure 4B:
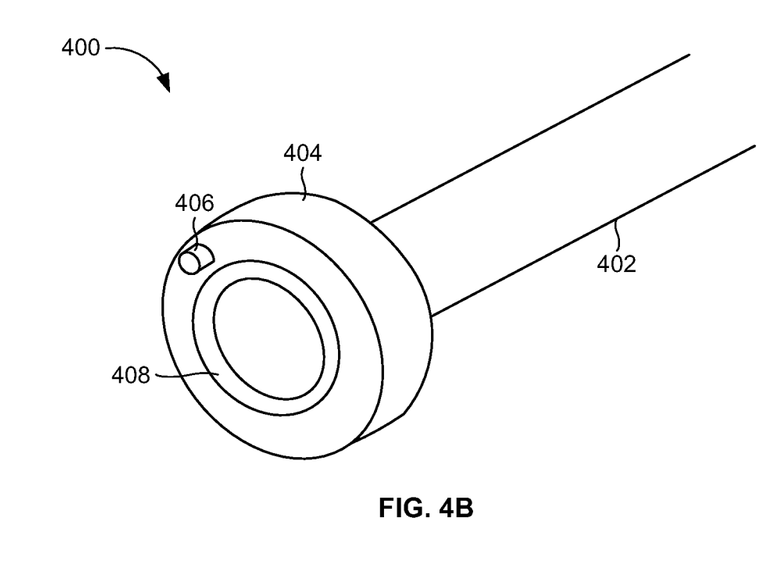
FIG. 4B illustrates a magnified view of the tool of FIG. 4A according to an embodiment herein.

FIG. 4A illustrates a perspective view of a tool 400 used in accordance with the anti back-out mechanism 116 of FIG. 1 according to an embodiment herein. FIG. 4B illustrates a magnified view of the tool 400 of FIG. 4A according to an embodiment herein. The tool 400 includes a cylindrical rod portion 402, a circular head 404, a peg 406, and an annular ring 408. The circular rod 402 is of uniform length. The circular head 404 is positioned at an end of the cylindrical rod portion 402. The tool 400 is adapted to rotate the anti back-out rings 116. The rod 402 may act as a hand tool to allow a surgeon to easily grip the tool 400 with just one hand. The peg 406 is positioned on the head 404 of the tool 400 and is dimensioned and configured to fit into the aperture 118 of the anti back-out ring 116 and to cause rotation of the anti back-out ring 116 within the channels 302. The rotation of the tool 400 causes the peg 406 to rotate the anti back-out rings 116. Accordingly, the surgeon may rotate and fix the anti back-out rings 116 into the channels 302 of the bone plate 100. The annular ring 408 is positioned on the circular head 404 and is dimensioned and configured to fit within the inner circumference defined by each anti back-out ring 116 (i.e., within circle 204). The bone screws 120 cover a portion of the channels 302 when fixed into the hole 114 at a variable angle (as shown in FIG. 3C). The tool 400 may comprise a handle (not shown) or other gripping means to facilitate easy rotation of the tool 400.

Figure 5:
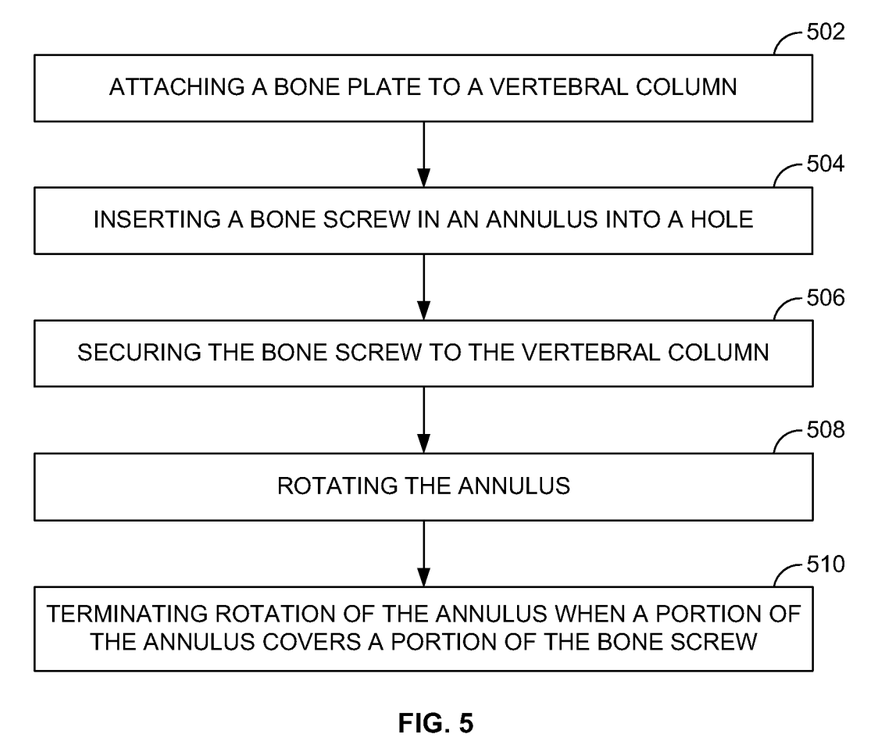
FIG. 5 illustrates a process flow illustrating a method of performing a surgical procedure according to an embodiment herein.

FIG. 5, with reference to FIGS. 1A through 4B, is a process flow diagram illustrating a method of performing a surgical procedure according to an embodiment herein, wherein the method comprises attaching (502) a bone plate 100 to a vertebral column, inserting (504) a bone screw 120 in an eccentrically shaped annulus (e.g., the anti back-out rings 116) into a hole 114, securing (506) the bone screw 120 to the vertebral column, rotating (508) the annulus 116, and terminating (510) rotation of the annulus 116 when a portion of the annulus 116 covers a portion of the bone screw 120.

In step 502, the bone plate 100 is attached to the vertebral column (e.g., through the bottom surface 106 of the bone plate 100). In step 504, the bone screw 120 is inserted in the anti back-out ring 116 into a hole 114. In step 506, the bone screw 120 is secured to the vertebral column. In step 508, the anti back-out ring 116 is rotated (e.g., through the help of the tool 400). In step 510, rotation of the anti back-out ring 116 is terminated when a portion of the of the anti back-out ring 116 covers a portion of the bone screw 120.

The bone plate 100 may be used as a bone securing plate for surgeries intended to stabilize one or more bones in the human skeletal system. The bone plate 100 may be used to stabilize two or more vertebrae until they fuse into one, or stabilize a fractured bone. The bone plate 100 with its inner anti back-out rings 116 may enable a surgeon to perform an additional step to secure two bones with the bone plate 100 and the bone screws 120, thus prevent the bone screws 120 from toggling, vibrating out over time, and/or their possible back-out of the bone plate 100 unless desired by the surgeon.

In another embodiment, the bone screws 120 may be secured from possible back-out and/or toggling within an anterior lumbar plate or a lateral lumbar plate. Accordingly, the bone plate 100 may be used as a cervical bone plate, an anterior lumbar plate, and/or a lateral lumbar plate. When the bone plate 100 is used as a lumbar plate, the size of the bone plate 100 may be approximately 20% to 140% of that of a corresponding cervical plate. The anterior lumbar plate and the lateral lumbar plate embodiments may stabilize long bone fractures due to their increased sizes.

The embodiments herein solve the problem of conventionally designed implants in which the rings tend to be small in size and may not necessarily reveal if they have secured the bone screw properly, whereas the rotation of anti back-out rings 116 clearly indicate whether the bone screws 120 are properly secured, for example through a post-operative x-ray due to the metallic materials used for constructing the rings 116 and bone screw 120. In addition, revising or removing the bone plate 100 is easier than other conventional implants because of the superior visibility and access to engage the locking anti back-out rings 116.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:
1. A system for providing stability to a vertebral column, said system comprising:
    a substantially rectangular plate comprising:
        a top surface;
        a bottom surface oppositely positioned from said top surface;

a plurality of projections extending from each corner and central side areas of said plate;

a plurality of openings extending from said top surface to said bottom surface through said plate; and a plurality of holes separate from said plurality of openings and configured in said plurality of projections and extending from said top surface to said bottom surface through said plate, wherein each hole of said plurality of holes are dimensioned and configured to accommodate a bone screw, wherein each said hole comprises:

an eccentrically-shaped anti back-out ring configured to rotate from an unlocked position to a locked position and comprising a thin end and a thick end, wherein said thick end comprises exactly one aperture; and an angled eccentrically-shaped sidewall contacting the anti back-out ring, wherein said anti back-out ring is a continuous structure and is rotatably seated adjacent to the sidewall in said hole, and wherein said thick end of said anti back-out ring covers a portion of a head of said bone screw upon said anti back-out ring being configured in said locked position.

2. The system of claim 1, wherein said plate is curved.

3. The system of claim 1, wherein said anti back-out ring is defined by an outer circular ring and an inner circular ring such that said thin end and said thick end define a non-uniform thickness between said outer circular ring and said inner circular ring for an entire continuous structure of said anti back-out ring, and wherein said outer circular ring and said inner circular ring do not share a same center point.

4. The system of claim 1, further comprising a tool configured to rotate said anti back-out ring from said unlocked position to said locked position and vice versa.

5. The system of claim 4, wherein said tool comprises:
a cylindrical rod portion;
a circular head positioned at an end of said cylindrical rod portion;
exactly one peg positioned on and extending from said circular head; and
an annular ring positioned on said circular head.

6. The system of claim 5, wherein said circular head comprises a diameter greater than a diameter of said cylindrical rod portion.

7. The system of claim 5, wherein said peg of said tool is dimensioned and configured to fit into said aperture of said anti back-out ring, wherein said annular ring is dimensioned and configured to fit in said anti back-out ring, and wherein rotation of said tool causes said peg to rotate said anti back-out ring.

8. The system of claim 1, wherein said substantially rectangular plate comprises any of a cervical bone plate, an anterior lumbar plate, and a lateral lumbar plate.

9. The system of claim 1, further comprising a channel adjacent to said sidewall, wherein said channel holds said anti back-out ring.

10. The system of claim 9, wherein said channel is dimensioned and configured to permit said anti back-out ring to rotate with respect to said sidewall.

11. The system of claim 9, wherein said channel comprises a notch, and wherein said anti back-out ring comprises a flared end that is dimensioned and configured to fit into said notch of said channel.

12. The system of claim 1, wherein said sidewall is angled.

13. The system of claim 1, wherein said anti back-out ring sits level within said hole.

14. The system of claim 1, wherein said continuous structure comprises a complete ring structure without having a gap along said ring structure.

15. The system of claim 1, wherein said anti back-out ring is "O" shaped.

16. The system of claim 1, wherein said aperture is positioned on an upper surface of said anti back-out ring.

17. The system of claim 1, wherein said plurality of openings are rectangular in shape.

* * * * *